United States Patent [19]

Devos

[11] Patent Number: 5,466,795

[45] Date of Patent: Nov. 14, 1995

[54] PROCESS FOR THE MANUFACTURE OF MANNITOL

[75] Inventor: Francis Devos, Morbecques, France

[73] Assignee: Roquette Freres, Lestrem, France

[21] Appl. No.: 90,615

[22] Filed: Jul. 12, 1993

[30] Foreign Application Priority Data

Jul. 22, 1992 [FR] France .................................. 92 09053

[51] Int. Cl.$^6$ ............................ C07H 1/06; C07C 31/18; C12P 19/24
[52] U.S. Cl. .............................. 536/125; 435/94; 568/852
[58] Field of Search ............................ 536/125; 568/852, 568/853, 854; 435/94

[56] References Cited

U.S. PATENT DOCUMENTS

| | | | |
|---|---|---|---|
| 2,985,589 | 5/1961 | Broughton et al. | 568/822 |
| 3,044,904 | 7/1962 | Serbia | 127/30 |
| 3,416,961 | 12/1968 | Mountfort et al. | 127/46.2 |
| 3,692,582 | 9/1972 | Melaja | 127/46.2 |
| 4,029,878 | 7/1977 | Kruse | 536/125 |
| 4,083,881 | 4/1978 | Takemura et al. | 536/125 |
| 4,157,267 | 6/1979 | Odawara et al. | 127/46.2 |
| 4,163,691 | 8/1979 | Devos et al. | 435/174 |
| 4,173,514 | 11/1979 | Kruse | 435/94 |
| 4,182,633 | 1/1980 | Ishikawa et al. | 127/46.2 |
| 4,226,977 | 10/1980 | Neuzil et al. | 536/127 |
| 4,292,451 | 9/1981 | DeBerardinis et al. | 568/863 |
| 4,293,346 | 10/1981 | Landis et al. | 127/46.2 |
| 4,332,623 | 6/1982 | Ando et al. | 127/46.2 |
| 4,405,455 | 9/1983 | Ando et al. | 210/191 |
| 4,412,866 | 11/1983 | Schoenrock et al. | 127/46.2 |
| 4,422,881 | 12/1983 | Devos et al. | 127/46.1 |
| 4,492,755 | 1/1985 | Horwath et al. | 435/94 |
| 5,049,494 | 9/1991 | Allenza | 435/105 |

FOREIGN PATENT DOCUMENTS

| | | |
|---|---|---|
| 0074713 | 3/1983 | European Pat. Off. . |
| 0115631 | 8/1984 | European Pat. Off. . |
| 0302970 | 2/1989 | European Pat. Off. . |
| 1295386 | 11/1972 | United Kingdom . |
| 1540556 | 2/1979 | United Kingdom . |
| 1596911 | 9/1981 | United Kingdom . |

OTHER PUBLICATIONS

J. Biol. Chem., 218, pp. 535 to 538; 1956.
Agr. Biol. Chem., vol. 31, No. 4, pp. 435 to 440; 1967.
J. Biol. Chem., 240, pp. 2367 to 2372; 1965.

Primary Examiner—Michael G. Wityshyn
Assistant Examiner—Everett White
Attorney, Agent, or Firm—Larson & Taylor

[57] ABSTRACT

A process for the manufacture of mannitol in which:

in a first step, a fructose syrup containing less than 15% glucose is subjected to an enzymatic isomerization using at least one enzyme capable of interconverting fructose and mannose, the enzymatic isomerization resulting in the production of a mixture of fructose and mannose containing at least 15% mannose, in a second step, the mixture of fructose and mannose is subjected to a chromatographic separation treatment so as to obtain at least two fractions one of which (fraction X1) is highly enriched with mannose and the other of which (fraction X2) is highly enriched with fructose, in a third step, fraction X2 is at least partially recycled to the top of the enzymatic isomerization step, in a fourth step, fraction X1, highly enriched with mannose, is hydrogenated so as to obtain a mannitol-rich syrup.

15 Claims, 2 Drawing Sheets

PROCESS FOR THE MANUFACTURE OF MANNITOL

The present invention relates to a process for producing mannitol.

The catalytic hydrogenation of mannose occurs with a stoichiometric yield and gives mannitol.

The catalytic hydrogenation of fructose also makes it possible to produce mannitol but the yield is not stoichiometric since the hydrogenation of fructose is not stereospecific and gives sorbitol in an equal amount.

Mannitol is widely used in the manufacture of sugar-free chewing gum, sweets or pharmaceutical excipients. However, the production of high-purity mannose is extremely difficult to achieve and is costly, and the manufacture of mannitol is only generally carried out industrially from fructose syrups, thereby generating a large quantity of sorbitol.

An old process consisted in hydrogenating an invert sucrose syrup consisting of equal parts of glucose and fructose and made it possible to obtain only a syrup with a mannitol content of about 25%.

A more recent process described in American Patent U.S. Pat. No. 4,029,878, filed in 1975, consisted in carrying out the chemical epimerisation of glucose to mannose, the hydrogenation of this epimerized syrup providing syrups with a mannitol content of about 30%.

An improvement in this process, which is described in American Patent U.S. Pat. No. 4,173,514, filed in 1977, consisted in isomerizing these epimerized syrups in order to convert a portion of the nonepimerized glucose to fructose. The thermodynamic equilibria for these reactions and the industrial conditions for their implementation lead to the production of ternary glucose/mannose/fructose mixtures in proportions of about 4/28/28 respectively which make it possible to obtain, by hydrogenation, syrups with a mannitol content of about 42%.

The hydrogenation of syrups with a high fructose content results, for its part, in syrups with a mannitol content of about 48%, and the hydrogenation of pure fructose would result in syrups with a mannitol content of about 50%.

However, these raw materials are relatively costly and do not allow mannitol to be manufactured under the best economic conditions.

All these processes have, in addition, the disadvantage of generating a large quantity of by-product containing essentially sorbitol, but also containing mannitol which cannot be crystallized and whose loss further reduces the yields. Thus, in the order in which they were described earlier, the processes described above make it possible to obtain only about 12%, 17.5%, 32%, 39% and 40% of pure crystallized mannitol, respectively, relative to the sugars used in the catalytic hydrogenation step.

This also means that the same process offering the highest yield, that is to say that consisting in hydrogenating fructose, nevertheless generates 1.58 kg of a by-product which is difficult to upgrade, containing 85% of sorbitol and 15% of mannitol for each kilogram of chemically pure crystallized mannitol produced by this process.

This latter process also suffers from the disadvantage of necessitating the use of a relatively expensive material: syrups with a very high fructose content. It therefore needed to be improved although more efficient in terms of yield.

Several years ago, PALLERONI and DOUDOROFF isolated, from a *Pseudomonas saccharophila*, an enzyme which they called mannose isomerase and which is capable of interconverting fructose and mannose in the respective proportions of 71/29 (J. Biol. Chem., 218, pages 535 to 548; 1956).

A similar enzyme has also been isolated by TAKASAKI from a *Streptomyces aerocolorigenes* (Agr. Biol. Chem., vol. 31, No. 4, pages 435 to 440; 1967) and by ANDERSON and ALLISON (J. Biol. Chem. 240, pages 2367 to 2372; 1965) from an *Aerobacter aerogenes* under the name of D-Lyxose isomerase. Much later, ALLENZA (U.S. Pat. No. 5,049,494, filed in 1989) used a mannose isomerase from *Pseudomonas cepacia*, extracted after disruption of the cell walls and then immobilized on an alumina support impregnated with polyethylenimine and cross-linked with glutaraldehyde, this in order to continuously isomerize a mannose-containing raw material such as the residual lyes from the paper-making industry, with the aim of manufacturing fructose economically. He then made the hypothesis that the fructose formed could be separated from mannose by a chromatographic technique or by separation using membranes. However, as regards the production of pure mannose, the preferred raw material for implementing his invention, he recommended isolating it from the other sugars by precipitation of its bisulphite derivative or of methylmannoside, which is a clear admission of the low efficiency of these chromatographic or membrane techniques.

In 1982, HORWATH (American Patent U.S. Pat. No. 4,492,755) had isomerized L-fructose to L-mannose by means of an L-mannose isomerase produced by a mutant of *Klebsiella aerogenes* and separated the mannose formed and the residual fructose by selective crystallization of the addition derivatives of these sugars with phenylhydrazine and regeneration of the mannose from its phenylhydrazone.

In 1981, KRUSE et al. (European Patent Application No. 74 713) recommended, for their part, enriching the mannose contained in a glucose syrup by precipitation in the form of a mannose/sodium chloride complex.

All these processes for purifying mannose involve chemical derivatives and are difficult to industrialize since the mannose must subsequently be regenerated.

The chromatographic separation of mixtures of glucose and fructose has been described for a long time and on many occasions, both on cationic resins and on zeolites. It makes it possible to prepare syrups with a very high fructose content. The glucose-enriched fraction is always eluted slightly before the fructose-enriched fraction. American Patent U.S. Pat. No. 3,044,904, filed in 1960, by CENTRAL AGUIRE SUGAR COMPANY, can thus be consulted with interest as regards the chromatography of mixtures of glucose and fructose on cationic resins, and American Patent U.S. Pat. No. 4,226,977, filed in 1976, by UNION OIL PRODUCTS, as regards the chromatography of these mixtures on zeolites.

The chromatographic separation of mixtures of glucose and mannose has also been described for a long time and on many occasions, on cationic resins such as zeolites, with the essential aim of producing syrups with a high mannose content, which are capable of providing, by hydrogenation, mannitol with a high yield. However, the chromatographic separation of these two sugars has proved to be very inefficient. In this case as well, the glucose-enriched fraction is always eluted slightly before the mannose-enriched fraction. British Patent No. 1,540,556, filed in 1977, by IMPERIAL CHEMICAL INDUSTRIES, can be consulted with interest as regards the chromatography of mixtures of glucose and mannose on cationic resins, and European Patent Application No. 115 631, filed in 1983, by UNION CARBIDE, as regards the chromatography of these mixtures on zeolites.

European Patent Application No. 302 970, filed in 1987, by UNION OIL PRODUCTS, relative to the separation of various aldohexoses and ketohexoses in fact clearly shows that while glucose separates slightly from mannose and more from fructose on zeolites, mannose and fructose are practically inseparable. The fructose/mannose selectivity of the adsorbent is indeed only 1.68 whereas it is 4.84 for fructose/glucose and 2.88 for mannose/glucose (4.84:1.68).

While an adsorbent selectivity of the order of 5 has brought about a real explosion in the manufacture of fructose syrups by chromatography of glucose/fructose mixtures, a selectivity of the order of 3 has however proved insufficient to bring about the development of the production of syrups with a high mannitose content from glucose/mannose mixtures, these syrups with a high mannose content having nevertheless to constitute the ideal raw material which permits the production of mannitol with a virtually stoichiometric yield.

Now, the applicant company has had the merit of finding that a selectivity as low as 1.68 could nevertheless be exploited in a process for the manufacture of syrups with a high mannose content, intended most particularly for the manufacture of mannitol by catalytic hydrogenation, so long as the syrups subjected to the chromatographic separation have at the same time a fructose content of at least 65%, a mannose content of at least 15% and a glucose content of less than 15%. These contents, as well as the contents appearing in the description of the present patent application which follows, unless otherwise stated, expressed by weight relative to the dry matter.

Figure 1:
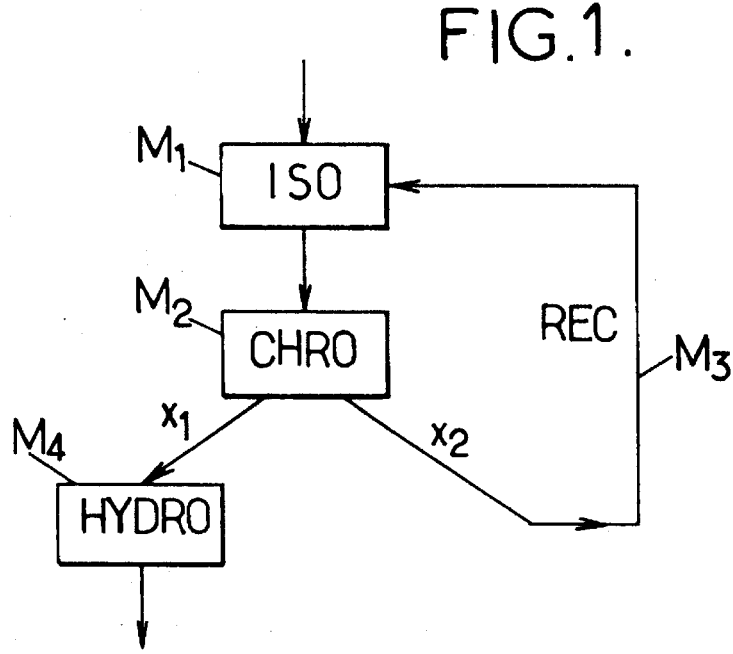
FIG. 1 is a schematic representation of the steps comprising the process of the invention.

The process for the manufacture of mannitol conforming to the invention comprises the following steps, which are restated schematically in FIG. 1:

in a first step M1, a fructose syrup containing less than 15% glucose is subjected to an enzymatic isomerization which results in the production of a mixture of fructose and mannose containing at least 15% mannose, in a second step M2, the abovementioned mixture is subjected to a chromatographic separation treatment which results in at least two fractions one of which is highly enriched with mannose (fraction X1) and the other of which is highly enriched with fructose (fraction X2), in a third step M3, fraction X2 is at least partially recycled to the isomerization step, in a fourth step M4, fraction X1, highly enriched with mannose, is subjected to a catalytic hydrogenation.

The fructose syrup may be obtained in a manner known per se by chromatography of glucose/fructose mixtures derived from invert sucrose or isomerized starch hydrolysates. It may also be obtained by hydrolysis of inulin. In both cases, it is advisable that this syrup does not contain more than 15% glucose which, being poorly separated from mannose, would adversely contaminate the fraction highly enriched with mannose which is derived from the chromatographic step.

This syrup contains more than 80%, preferably more than 85% and still more preferably more than 90% fructose.

According to an advantageous variant of the process according to the invention, the fructose syrup used as raw material is a syrup obtained by chromatography of isomerized starches hydrolysates and it contains more than 95% fructose.

The enzymatic isomerization of fructose to mannose is carried out continuously or batchwise according to processes known per se and described for example by PALLERONI and DOUDOROFF (J. Biol. Chem., 218, pages 535 to 548; 1956), as regards batch isomerization, and by ALLENZA (American Patent U.S. Pat. No. 5,049,494) as regards the continuous isomerization by an immobilized enzyme.

A convenient means is to allow a bacterial slurry, obtained by centrifugation or filtration of a culture broth of *Pseudomonas saccharophila*, to act on a fructose syrup with a dry matter content of about 40%, at a pH of about 7.5 and at a temperature of 30° to 50° C., and preferably of about 40° C. Care should be taken in this case to introduce the bacteria in sufficient quantity so that the isomerization reaction proceeds at a speed such that a percentage of at least 15% mannose is achieved in a maximum of 24 to 30 hours, otherwise it would become necessary to introduce an antiseptic agent into the isomerization reactor. The discovery of a more thermostable mannose isomerase could make it possible to avoid this constraint.

Advantageously, the isomerization of fructose to mannose is carried out continuously. In this case, the enzyme can be extracted from bacteria by sonicating them and the crude extract can be adsorbed or attached via covalent bonding onto an activated inorganic support as described in American Patent U.S. Pat. No. 5,049,494.

Another process for immobilizing the enzyme, and which is preferably used in the process conforming to the invention, consists in immobilizing the whole cells inside a protein network consisting for example of gelatine cross-linked by means of a bifunctional coupling agent such as glutaraldehyde. A description of such a method of immobilizing the bacterial cells is found in American Patent U.S. Pat. No. 4,163,691 which is held by the applicant company. Such a process immobilizes the entire enzymatic potential contained inside the cells but in this case, the lack of production of undesirable compounds is due to the purity of the substrate which essentially contains only fructose.

Care should however be taken to ensure that the immobilized microbial mass does not contain glucose isomerase in substantial quantity, otherwise a portion of the fructose would be isomerized to glucose, thereby greatly impairing the efficiency of the process. If such is however the case, a small amount of calcium is added to the fructose syrup and this inhibits the glucose isomerase without affecting the mannose isomerase.

Carrying out the isomerization at a pH substantially greater than 7.5 should also be avoided since in this case a portion of the fructose would be isomerized to glucose by alkaline chemical catalysis.

Preferably, the immobilized enzyme is used in a reactor in the form of a column which is heat-insulated or thermostated and provided with a porous base. The fructose syrup is percolated through the particles of this enzyme at a temperature of 30° to 50° C. at a flow rate such that a proportion of mannose of between 15 and 29% is obtained at the outlet.

The enzymatic activity trapped inside the isomerization reactor is such that its concentration makes it possible to obtain the abovementioned mannose percentage with a syrup residence time inside the reactor preferably of between 2 and 20 hours.

The fructose syrup enriched with mannose after the isomerization step is then subjected to chromatographic fractionation. This chromatographic fractionation is carried out in a manner known per se, batchwise or continuously (simulated fluidised bed), on adsorbents of the highly acidic cationic resin type preferably charged by means of alkali or alkaline-earth metal ions, or on cationic zeolites charged with the same ions.

Examples of such processes are described especially in U.S. Pat. Nos. 3,044,904; 3,416,961; 3,692,582; FR 2,391, 754; 2,099,336; U.S. Pat. Nos. 2,985,589; 4,024,331; 4,226, 977; 4,293,346; 4,157,267; 4,182,633; 4,332,623; 4,405, 455; 4,412,866 and 4,422,881.

According to a preferred embodiment, the chromatographic fractionation is carried out using the process and apparatus described in American Patent U.S. Pat. No. 4,422, 881 which is held by the applicant company.

Whichever chromatographic process is chosen, as regards the absorbent, a strong cationic resin employed in the calcium form and cross-linked with about 4 to 10% divinylbenzene is preferably used. The resins are advantageously of homogeneous particle size which is between 100 and 800 microns.

The choice of parameters for the chromatographic fractionation, among which there may be noted more particularly the elution rate, the isomerized fructose syrup supply rate, the mannose-enriched fraction extraction rate, the flow rate of the fructose-enriched fraction and the composition of the zones of desorption, adsorption and enrichment, is explained and illustrated in the examples.

The choice of these parameters is made in such a manner that fraction X1 has a mannose level, the percentages being expressed by weight relative to the dry matter, of between 30 and 80%, preferably of between 35% and 70% and still more preferably of between 40% and 60%, as well as a glucose level of less than 15% and preferably less than 10%.

To arrive at this result, these parameters are chosen as follows, when the chromatographic fractionation is carried out using the process and apparatus described in U.S. Pat. No. 4,422,881 and when the adsorbent used is a cationic resin of small particle size cross-linked with 6% divinylbenzene and when the said resin is used in the calcium form:

elution rate of 70 to 700 l/h/m$^3$ of adsorbent, isomerized syrup supply rate of 10 to 100 l/h/m$^3$ of adsorbent, mannose-enriched fraction extraction rate: 80 to 800 l/h/m$^3$ of adsorbent, fructose-enriched fraction extraction rate: 20 to 200 l/h/m$^3$ of adsorbent.

The chromatographic fractionation step provides the simultaneous production of fraction X2, highly enriched with fructose, and optionally a glucose-containing fraction X3 which exists as impurity in the fructose syrups and which should be periodically purged so that glucose does not accumulate and that its content does not exceed, after recycling of fraction X2 into the fructose syrup used as raw material, a value of 15% in the syrup subjected to chromatographic fractionation.

Fraction X2, highly enriched with fructose, preferably has the following composition, the percentages being expressed by weight relative to the dry matter:

76 to 97% fructose, 2 to 24% mannose, 0 to 15% glucose.

In conformity with the invention, this fraction X2 which is highly enriched with fructose is recycled to the isomerization step.

Using the process conforming to the invention, which takes advantage of the combined benefits of the isomerization of fructose, the chromatographic separation of the isomerized syrup and the recycling of the nonisomerized separated fructose, it becomes possible to convert fructose to mannose with a very high yield.

The mannose level of fraction X1, which is insufficient in itself to give mannitol with a good yield by hydrogenation, is nevertheless sufficient given that the accompanying impurity, fructose, also generates mannitol by hydrogenation, thus compensating the low fructose/mannose selectivity of the adsorbent.

Furthermore, the mannitol levels reached after the hydrogenation step make it possible to crystallize it in the pure state in a single crystallization operation. It is even possible, by completely drying this fraction X1, to obtain, with a total yield, a technical mannitol of very high purity. The processes known until now, including the process for the direct hydrogenation of the isomerized fructose syrups, did not allow a sufficient mannitol level to be obtained and required several successive recrystallizations of mannitol to be carried out.

Thus, a syrup with 25% mannitol obtained from sucrose for example required three successive crystallizations to be carried out and a syrup with a mannitol level of less than 65% required two successive crystallizations to be carried out.

One of the essential advantages of the process according to the invention lies in the fact that it makes it possible to obtain chemically pure crystallized mannitol so long as the mannose level of fraction X1 is greater than 30%, which results in a mannitol level, after hydrogenation, greater than 65%.

Using the process according to the invention, and by carrying out several successive crystallizations on the mother liquors, which is made possible by the high level of the syrups obtained after hydrogenation, the crystallized mannitol yield relative to the sugar (fructose) used can be as high as 70% and more, the production of 1 kg of mannitol now generating the production of only 0.430 kg of a by-product containing 85% sorbitol, which is equivalent to a reduction in the production of by-product by a factor of 3.3 relative to a best prior art process, using fructose as raw material but with a yield of 40%.

EXAMPLES

Isomerization

A strain ATCC 15946 of *Pseudomonas saccharophila*, adapted to culturing on fructose medium, was cultivated under the conditions described by PALLERONI and DOUDOROFF.

The cells were centrifuged and the bacterial slurry obtained was supplemented with a solution of gelatin containing 50% dry matter in the proportions of 100 kg of gelatin solution per 200 kg of slurry.

The resulting product was injected into a die perforated with 400 holes of 500 microns in diameter immersed in cold water, in conformity with the process described in French Patent 2,353,562.

Cross-linking of the gelatin was carried out via a 15-hour contact of the bacterial slurries thus extruded in a 1% glutaraldehyde solution maintained at a temperature of 2° C.

The threads formed were cut into pieces of an average length of 2 mm and were immediately loaded onto thermostatted columns at 35° C., of a height of 200 cm and a diameter of 25 cm.

A fructose syrup, obtained by remelting of crystallized fructose, having a dry matter content equal to 40% and a pH of 7.0, was percolated through these columns. The columns were supplied at a rate of 30 liters/hour of fructose syrup and an isomerized fructose syrup containing 25% mannose and 75% fructose was recovered at the bottom of these columns.

The syrup obtained was deionized and then concentrated to a dry matter content of 53%.

Chromatographic Separation

Fractionation of the mannose-rich isomerized syrup was carried out in the continuous chromatographic separation installation of which the details of construction and operation are described in American Patent U.S. Pat. No. 4,422,881, these details being restated here only in terms of what is necessary for understanding the process. This installation comprises, as shown in FIG. 2 of American patent (restated here at FIG. 2 and for whose detailed explanation reference can be made to the said American patent), eight columns or stages C 1 to C 8 of 200 liters each, filled with strong cationic resin permuted in the calcium form and with a particle size of between 200 and 400 microns of the DUO-LITE C 204–2078 type.

Figure 3:
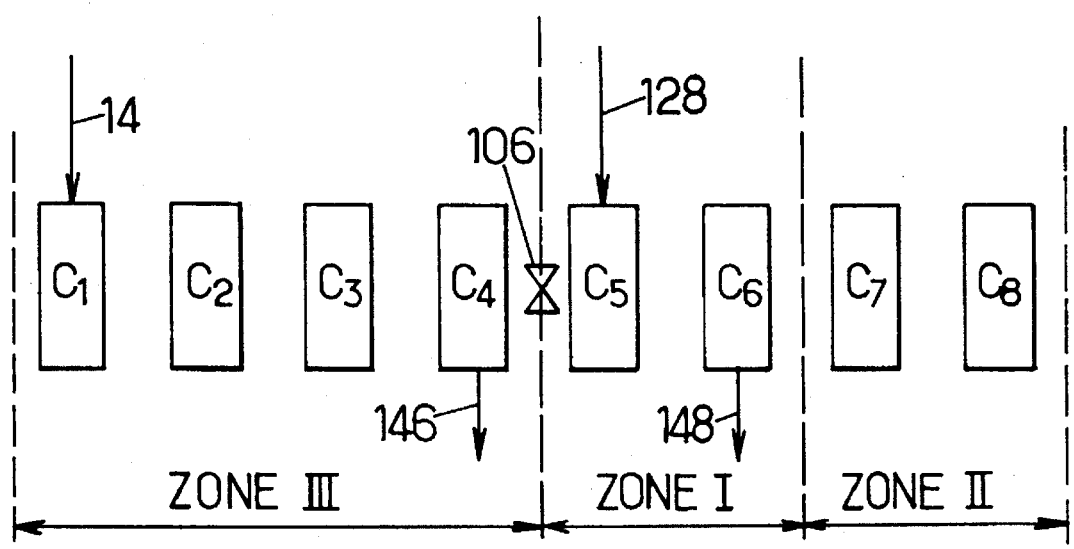
FIG. 3 is a schematic representation of the installation according to FIG. 2, showing Zones I, II and III.
Figure 2:
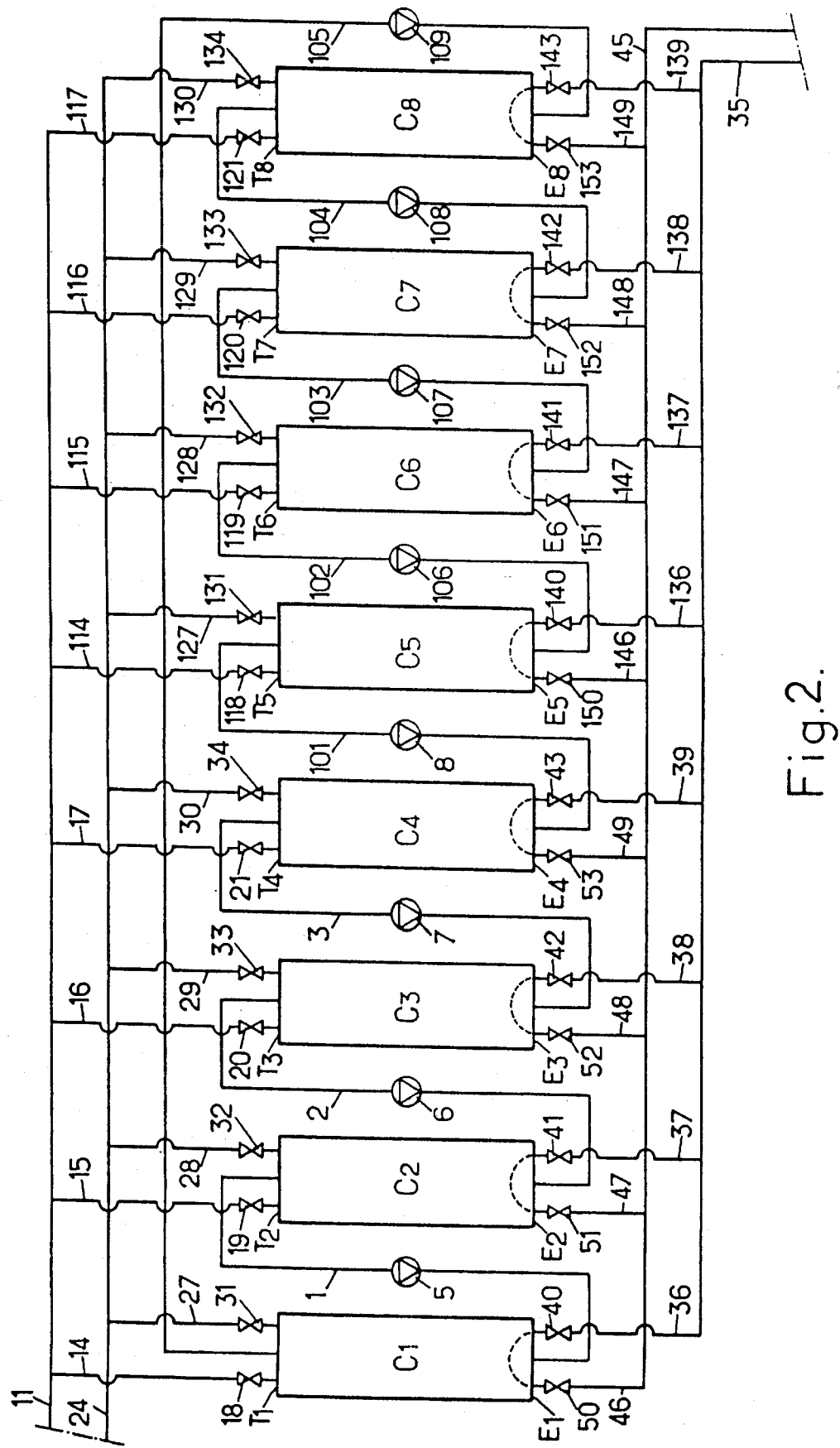
FIG. 2 is a schematic representation of the continuous chromatographic separation installation shown in FIG. 2 of U.S. Pat. No. 4,422,881.

By adjusting the solenoid valves, there is established in this installation a zone I of desorption comprising two stages, a zone II of adsorption comprising two stages and a zone III of enrichment and separation of the relatively less adsorbed mannose and of the relatively more adsorbed fructose comprising four stages as shown in FIG. 3, which is a schematic representation of the installation according to FIG. 2 and in which only the following are represented columns C 1 to C 8, the device for closing, in this case, the solenoid valve 106, the pipings for supplying water and mannose-rich isomerized syrup to be fractionated, which are shown in 128 and 14 respectively, and the piping 148 for extracting fructose-enriched syrup (fraction X2) on the one hand, and the piping 146 for extracting mannose (fraction X1).

The device for closing 106 maintains, in the configuration adopted, a complete tightness between, on the one hand, the zone III, which is a zone of enrichment at the end of which the mannose-enriched fraction is recovered and, on the other hand, the zone I of desorption of fructose, a zone at the fore-part of which the water for desorption is introduced.

This device for closing determines the direction of passage of the liquid phase over the selective adsorbent.

A timer adjusted to 1500 seconds ensures, for the flow rates indicated in Table I, a supply of water over the first column of zone I of desorption of the entire fructose, and a supply of a volume of mannose-rich isomerized syrup over the first stage of zone III which is compatible with the volume of adsorbent and its adsorption capacity, so as to obtain a mannose extraction yield at least equal to 7.5% of the mannose present in the isomerized syrup and that at a mannose level at least equal to 40%. At the end of the 1500 seconds, all the inlets and outlets, as well as the device for closing 106, are shifted one stage to the right.

The abovementioned extraction and purity levels are kept constant by adjusting the output of the pump (not shown) for extracting the adsorbed fructose. The discharge of fraction X1, optionally preceded by a fraction X3 containing a small amount of glucose, occurs at atmospheric pressure and its steady rate results from the difference between the supply rate and the extraction rate.

The mannose-rich isomerized syrup, which is introduced into the installation at the top of the zone of enrichment and separation III, has a dry matter content of 53%. The temperature inside the separating columns is kept at about 70° C.

The mannose-enriched fraction X1 as well as optionally the fraction X3 are preceded by a pure water fraction which has been used to desugar the column during the preceding cycle. This pure water fraction is advantageously removed during the first eighteen minutes of each cycle, thus making it possible to substantially increase the concentrations of the mannose-enriched fractions.

Table I below shows, for various conditions for operating the installation, the levels and concentrations obtained for the two fractions X1 and X2.

The preferred conditions for carrying out the chromatographic fractionation are those for which the mannose content of fraction X1 is between 40 and 60%. Such a mannose level is sufficient to provide, after hydrogenation, syrups with a mannitol content greater than 70%, which level it is not essential to exceed in order to obtain pure crystallized mannitol without having to carry out a recrystallization.

Moreover, under these conditions, the mannose extraction yield, which may be expressed as the ratio of the weight of pure mannose extracted in fraction X1 to the weight of pure mannose contained in the supply syrup, is much higher.

TABLE I

| | | | | |
|---|---|---|---|---|
| Rate for supplying the syrup containing 53% M.S. | 60 | 60 | 60 | 60 |
| Rate for supplying water (l/h) | 372 | 372 | 372 | 372 |
| Flow rate of the mannose-enriched fraction (l/h) | 332 | 362 | 371 | 380 |
| Flow rate of the fructose-enriched fraction (l/h) | 100 | 70 | 61 | 52 |
| Dry matter supplied in kg/h | 40 | 40 | 40 | 40 |
| MANNOSE-RICH FRACTION | | | | |
| % Dry matter after removal of excess water (18 min) | 1% | 10.6% | 15.2% | 20% |
| Dry weight | 0.925 kg | 11.2 kg | 16.8 kg | 23.2 kg |
| Mannose level (%) | 81 | 60 | 51 | 40 |
| Fructose level (%) | 19 | 40 | 49 | 60 |
| Mannose extraction yield | 7.5% | 67.2% | 85.7% | 92.8% |
| FRUCTOSE-RICH FRACTION | | | | |
| Dry matter | 34% | 35.8% | 33.5% | 28.5% |
| Dry weight | 39.075 | 28.8 kg | 23.2 kg | 16.8 kg |
| Mannose level (%) | 23.6 | 11.4 | 6.2 | 4.2 |

TABLE I-continued

| | | | | |
|---|---|---|---|---|
| Fructose level (%) | 76.4 | 88.6 | 93.8 | 95.8 |
| Mannitol level after hydrogenation | 90.5 | 80 | 75.5 | 70 |

The fructose-enriched fraction may be isomerized, under the conditions already discribed above, separately from the fructose syrup used as raw material, but it can also be mixed with this raw material and this mixture can be isomerized as a whole.

The mannose-rich fraction X1 is hydrogenated in a manner known per se. It is first concentrated to a dry matter content of 40% and then hydrogenated at a temperature of 140° C. at a hydrogen pressure of 50 bars in the presence of RANEY NICKEL catalyst.

In all cases, syrups were obtained whose mannitol level is greater than 70%, as also shown in Table I.

I claim:

1. Process for the manufacture of mannitol comprising:

in a first step, subjecting a fructose syrup containing less than 15% glucose to an enzymatic isomerization using one mannose isomerase capable of interconverting fructose and mannose, the said enzymatic isomerization resulting in the production of a mixture of fructose and mannose containing between 15% and 29% of mannose, in a second step, subjecting the said mixture to a chromatographic separation treatment so as to obtain at least two fractions one of which (fraction X1) is highly enriched with mannose and the other of which (fraction X2) is highly enriched with fructose, in a third step, at least partially recycling fraction X2 to the top of the enzymatic isomerization step, in a fourth step, hydrogenating fraction X1, highly enriched with mannose, so as to obtain a mannitol-rich syrup capable of being crystallized in a single crystallization operation.

2. Process according to claim 1, wherein the fructose syrup contains more than 80% of fructose.

3. Process according to claim 1, wherein the fructose syrup contains more than 85% of fructose.

4. Process according to claim 3, wherein the fructose syrup contains more than 90% of fructose.

5. Process according to claim 1, wherein the mixture subjected to the chromatographic separation treatment has a fructose content of at least 65%, a glucose content of less than 15%, and a mannose content of between 15% and 29%.

6. Process according to claim 1, wherein the enzymatic isomerization of the fructose syrup is carried out batchwise or continuously at a pH of about 7.5 and at a temperature of 30° to 50° C.

7. Process according to claim 6, wherein the enzymatic isomerization of the fructose syrup is carried out batchwise or continuously at a pH of about 7.5 and at a temperature of 30° to 50° C., in the presence of calcium ions.

8. Process according to claim 1, wherein the chromatographic treatment is carried out under conditions such that fraction X1 has a mannose level of between 30 and 80%, as well as a glucose level of less than 15%.

9. Process according to claim 8, wherein the chromatographic treatment is carried out under conditions such that fraction X1 has a mannose level of between 35 and 70%, as well as a glucose level of less than 15%.

10. Process according to claim 9, wherein the chromatographic treatment is carried out under conditions such that fraction X1 has a mannose level of between 40 and 60%, as well as a glucose level of less than 15%.

11. Process according to claim 8, wherein the chromatographic treatment is carried out under conditions such that fraction X1 has a mannose level of between 30 and 80%, as well as a glucose level of less than 10%.

12. Process according to claim 11, wherein the chromatographic treatment is carried out under conditions such that fraction X1 has a mannose level of between 35 and 70%, as well as a glucose level of less than 10%.

13. Process according to claim 12, wherein the chromatographic treatment is carried out under conditions such that fraction X1 has a mannose level of between 40 and 60%, as well as a glucose level of less than 10%.

14. Process according to claim 1, wherein the chromatographic treatment is carried out under conditions such that fraction X2 has a fructose content of between 76 and 97%, a mannose content of between 2 and 24% and a glucose content of between 0 and 15%.

15. Process according to claim 1, wherein the mannitol-rich syrup obtained has a mannitol level greater than 65%.

* * * * *

UNITED STATES PATENT AND TRADEMARK OFFICE
CERTIFICATE OF CORRECTION

PATENT NO. : 5,466,795
DATED : November 14, 1995
INVENTOR(S) : DEVOS

It is certified that error appears in the above-indentified patent and that said Letters Patent is hereby corrected as shown below:

In Fig. 3, change "106" to --8--.

In Fig. 3, change "128" to --127--.

In Fig. 3, change "146" to -- 39--.

In Fig. 3, change "148" to --147--.

In Column 7, Line 38, change "106" to --8--.

In Column 7, Line 40, change "128" to --127--.

In Column 7, Line 42, change "148" to --147--.

In Column 7, Line 43, change "146" to --39--.

In Column 7, Line 45, change "106" to --8--.

Signed and Sealed this

Twenty-third Day of July, 1996

Attest:

BRUCE LEHMAN

Attesting Officer

Commissioner of Patents and Trademarks